United States Patent [19]
Cortes et al.

[11] Patent Number: 5,679,255
[45] Date of Patent: Oct. 21, 1997

[54] MICROCOLUMNS FOR CHROMATOGRAPHY AND METHOD FOR MAKING SAME

[75] Inventors: Hernan J. Cortes; Curtis D. Pfeiffer, both of Midland, Mich.

[73] Assignee: The Dow Chemical Company, Midland, Mich.

[21] Appl. No.: 902,144

[22] Filed: Jun. 22, 1992

[51] Int. Cl.$^6$ ................................................. B01D 15/08
[52] U.S. Cl. ........................................ 210/656; 210/198.2
[58] Field of Search ................................ 210/635, 656, 210/198.2; 141/12, 73, 80

[56] References Cited

U.S. PATENT DOCUMENTS

| | | | |
|---|---|---|---|
| 4,483,773 | 11/1984 | Yang | 210/656 |
| 4,793,920 | 12/1988 | Cortes | 210/198.2 |

OTHER PUBLICATIONS

Ghijs, et al., "Experiments with Size-Exclusion Material in Microchromatography" *Journal of High Resolution Chromatography*, 13, 651–653, Sep. 1990.

Kennedy et al., "Efficiency of Packed Microcolumns Compared with Large-bore Packed Columns in Size-Exclusion Chromatography", *Journal of Microcolumn Separations*, 2, 120–126 (1990).

Jinno, et al., "Application to Gel Permination Chromatography of Micro High Performance Liquid Chromatography", *Analytical Letters*, 13(B8), 673–681, (1980).

Takeuchi, et al. "Separation of Oligomers by High-Performance Micro Gel Permeation Chromatograpy", *Journal of Chromatography*, 257, 327–335 (1983).

Takeuchi, et al. "Microcolumn High-Performance Size-Exclusion Chromatography Separation of Proteins", *Journal of Chromatograpy*, 351, 295–301 (1986).

Takeuchi, et al. "Temperature Effects in Microcolumn Size Exclusion Chromatography" *Journal of Liquid Chromatography*, 12(6), 987–996, (1989).

Snyder, Introduction to Modern Liquid Chromatography, 1979, John Wiley & Sons, pp. 194–195, 202–218, & 488–494.

Foley, "Equations for Calculations of Chromatographic Figures of Merit for Ideal and Skewed Peaks", 55 Analytical Chemistry, pp. 730–736 Apr. 1983.

Wilke, "Correlation of Diffusion Coefficients in Dilute Solutions" Am. Inst Chem Eng. J., 1, pp. 264–270, Jun. 1955.

Snyder, Introduction to Modern Liquid Chromatography, 1979, John Wiley & Sons, pp. 365–370 and 378–381.

*Primary Examiner*—Ernest G. Therkorn

[57] ABSTRACT

Highly efficient microcolumns suitable for use in chromatography, especially size excusion chromatography, are presented along with the method for making them. The method involves first obtaining a microcolumn having a first end and a second end, said microcolumn having an inner diameter of less than 1 mm. Then a slurry is prepared containing a packing material and a liquid solvent, said slurry having a concentration of more than 10 milliliters of solvent per gram of packing material. A retaining means is placed at the second end of the microcolumn, said retaining means being effective for retaining the packing material while allowing the liquid solvent to pass through the retaining means. The slurry is then added to the first end of the microcolumn at a constant pressure, said pressure being less than about 680 atmospheres. After a length of column suitable for use in chromatography has been filled, the addition of the slurry is stopped. The column is allowed to slowly decompress by allowing the solvent to exit the second end of the column.

12 Claims, 3 Drawing Sheets

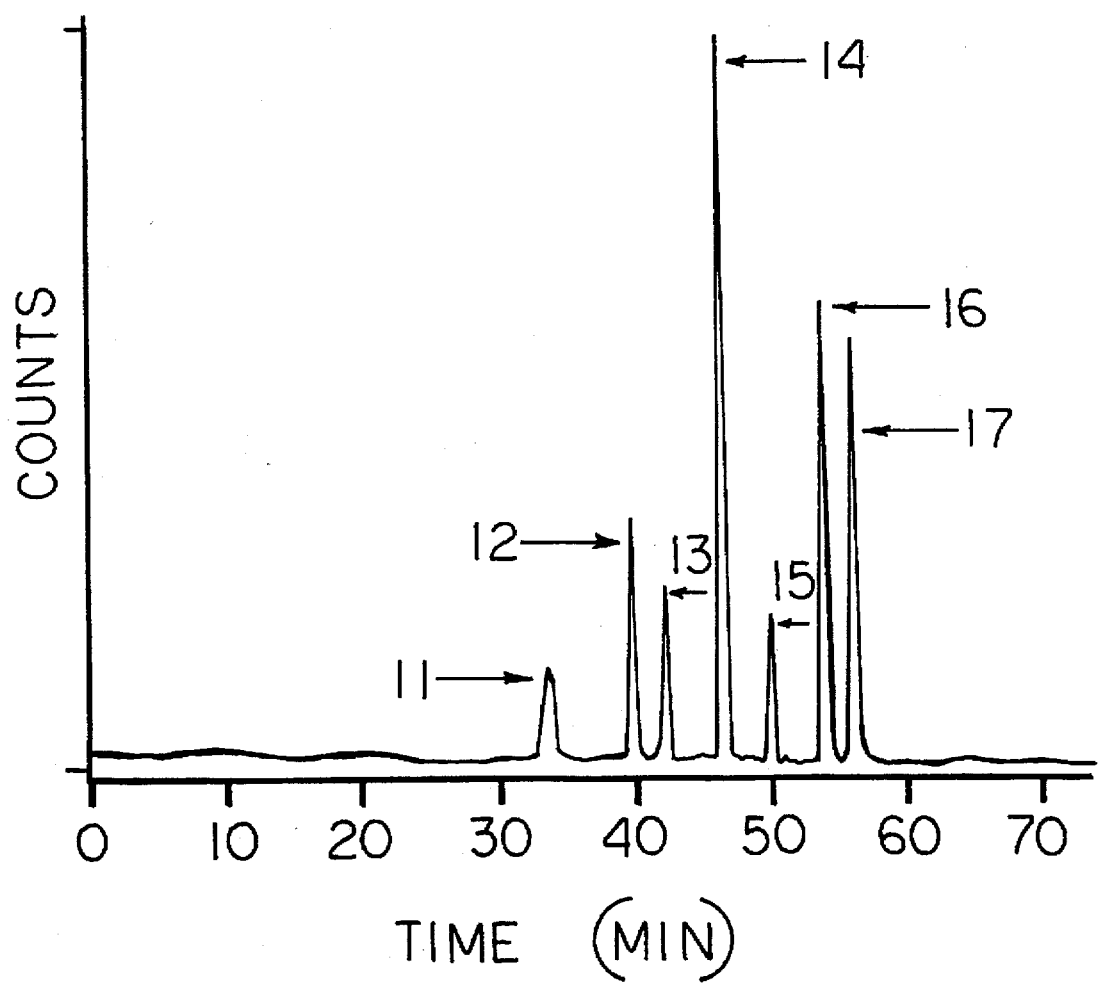

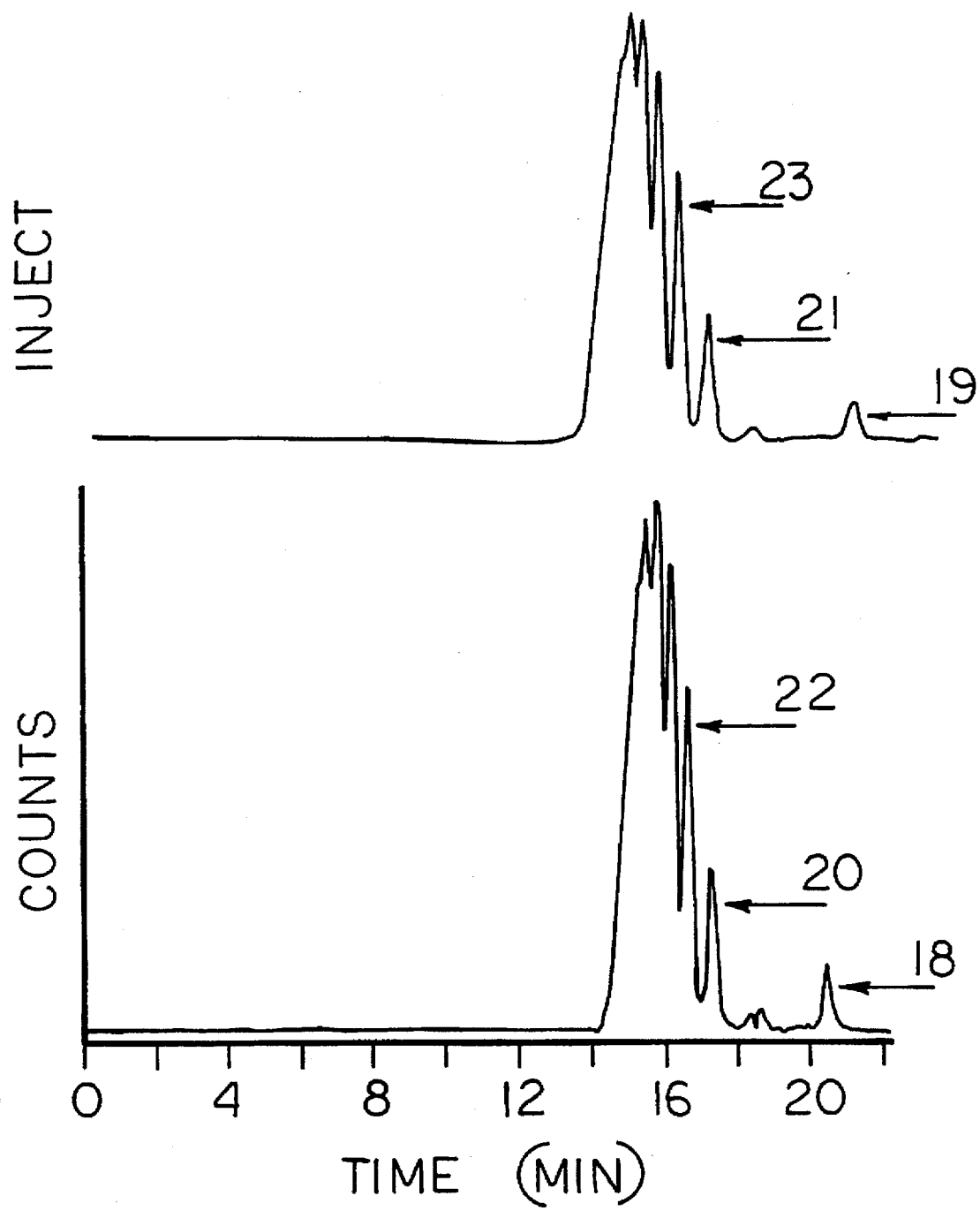

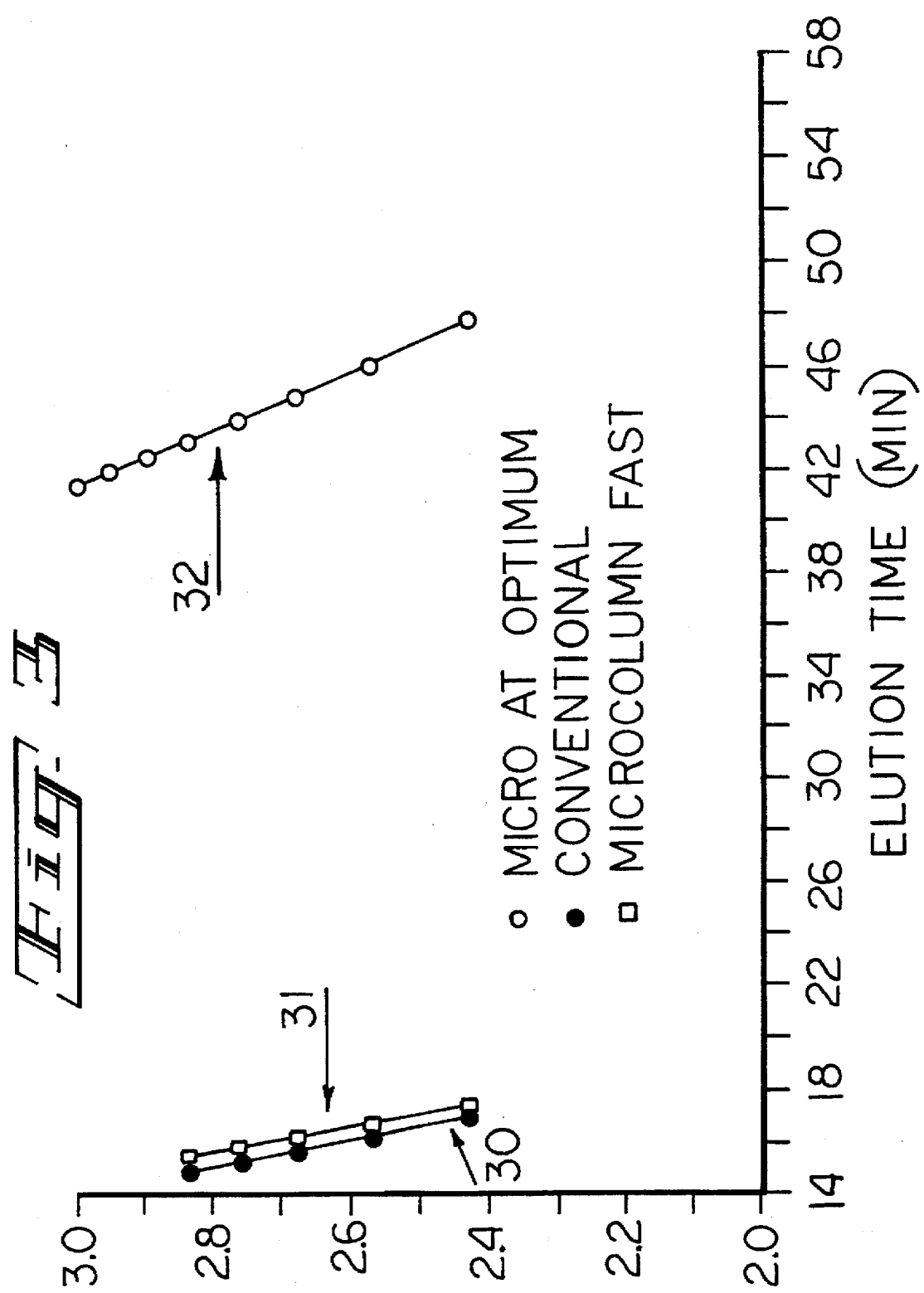

MICROCOLUMNS FOR CHROMATOGRAPHY AND METHOD FOR MAKING SAME

BACKGROUND OF THE INVENTION

This invention relates to improved chromatographic microcolumns and the process for making them. More particularly this invention relates to size exclusion chromatography microcolumns and the process for making them.

Size exclusion chromatography (SEC) offers unique selectivity not available in other separation modes, as components are separated on the basis of their hydrodynamic volume in solution, which is related to the molecule's shape and molecular weight. Separations in SEC are governed by the components' ability to migrate into pores of the stationary phase and any other interactions with the stationary phase are intentionally minimized. Accordingly, the smaller the component, the more pores of the stationary phase the component will enter, and the longer it will take for the component to elute through the column.

Consequently, the time it takes a component to elute through the column is controlled by the size of the component and the size and number of the pores in the packing material available for the components to enter.

Modifying the eluent does not produce significant results in SEC so increasing column efficiency has become the primary means of increasing resolution.

One method of increasing column efficiency in SEC has been to couple two or more column segments together. Deviations from theoretical efficiency are observed, however, due to band broadening caused by the variable velocity experienced by the band as a result of traveling between packed columns and the unpacked tubing used to couple the columns. Furthermore, coupling columns is not a completely adequate option as the cost may be prohibitive, since each column costs approximately $800 to $1500.

Another approach at increasing resolution for SEC uses microcolumns. Miniaturization of chromatographic systems offer many advantages, including lower cost per column and the ability to prepare longer columns. As column diameters decrease, however, it becomes more difficult to pack in a uniform reproducible manner. A column which is not uniformly packed, both along its length and across its diameter, will not be an efficient column. Thus, improved methods of loading the packing material into the columns have been sought.

Microcolumn SEC (micro SEC) was first investigated by Takeuchi et al., 257 *Journal of Chromatography*, 327 (1983). In that work epoxy resin oligomers were separated using manually packed short column segments connected in series.

Kennedy et al., 2 *Journal of Microcolumn Separations*, 120 (1990) have recently demonstrated that efficient micro SEC columns with an inside diameter of 28 to 50 μm could be packed with silica-based particles. These columns yielded more efficient separations than those obtained using conventional-size silica based SEC columns.

In general, high pressures (e.g. greater than 400 atm) are used to obtain efficient silica-based microcolumns. The use of high pressures is not always acceptable when the packing material is a porous polymeric material, however. Porous polymeric materials become more fragile with increasing pore size, and tend to swell to a larger extent than silica based particles. Thus, when the porous polymeric materials are packed at a high pressure, they are more likely to be damaged than silica-based particles.

It is therefore an objective of the present invention to provide a method for loading a polymeric packing material into microcolumns to form a microcolumn suitable for use in size exclusion chromatography.

It is also an objective of the present invention to provide a method for loading a polymeric packing material into microcolumns to form a microcolumn suitable for use in other types of chromatography.

It is another objective to provide microcolumns suitable for use in chromatography which exhibit improved column efficiency.

It is another objective to provide microcolumns suitable for use in size exclusion chromatography which exhibit improved column efficiency.

Additional advantages and features of the invention will become apparent from a reading of the detailed description of the invention and the examples which make reference to the following set of drawings:

BRIEF DESCRIPTION OF THE DRAWINGS

FIG. 1 is a copy of a chromatogram obtained using a microcolumn 1 meter in length and packed at 170 atm with a slurry ratio of 20 milliliters of solvent per gram of packing material.

FIG. 2 is a copy of two chromatograms, the first being obtained from a conventional-size chromatography column and the second being obtained from the same column as in FIG. 1 operated at a high linear velocity to produce retention times similar to that achieved by the conventional-size column.

FIG. 3 is a depiction of the calibration curves using polystyrene 580 on a conventional-size column, on a 1 meter microcolumn operated at a high linear velocity and on a 1 meter microcolumn operated at an optimum linear velocity.

SUMMARY OF THE INVENTION

The present invention is microcolumns packed with a polymeric material suitable for use chromatography and a method for making same. The method comprises preparing a dilute slurry of the polymeric packing material in a liquid solvent. Next, a retaining means is placed at one end of a column having an inner diameter of less than about 1 mm, the retaining means being effective for retaining the polymeric material while allowing the liquid solvent to pass. Then the dilute slurry is added to the column at a constant, relatively low (e.g. less than 680 atmospheres) pressure. The addition of the slurry is stopped after a length of column has been filled with packing material and the solvent remaining in the microcolumn is allowed to exit the column through the retaining means thereby reducing the pressure inside the microcolumn. This method produces stable microcolumns characterized by their increased column efficiency.

DETAILED DESCRIPTION OF THE INVENTION

In the preferred embodiment of the method of the present invention, a microcolumn is initially obtained. For purposes of this invention a microcolumn is considered to be any column having an inside diameter of approximately 1 mm or less. Most preferably, the column will have an inside diameter of 250 μm. This column may be constructed from materials such as glass, stainless steel, glass lined stainless steel, or fused-silica lined stainless steel, but it is preferred that they are constructed from fused silica.

Next, the obtained microcolumn is equipped with a retaining means at the exit end of the column. The retaining means is preferably a ceramic frit formed in situ in accordance with U.S. Pat. No. 4,793,920 to Cortes et al., but any retaining means which allows solvent to pass while retaining solid particles can be used. Furthermore, the retaining means should be capable of remaining within the end of the column at any pressure to which the microcolumn might be subjected.

Next, a relatively dilute slurry comprising packing material and a liquid solvent is prepared. The slurry should have a ratio of milliliters solvent to grams packing material of at least 10:1. It is preferred that the slurry ratio be between 10:1 and 40:1. Even more preferably, the ratio is between 25:1 and 40:1.

The packing material used to make up the slurry can be any polymeric material and is chosen according to the intended use of the column. Moreover, the size of the particles of packing material can be altered according to the needs of the finished column. There are many different chromatographic applications and the packing material of the column should be selected to meet the needs of each. In the preferred mode, the column is used for size exclusion chromatography and the packing material is styrene-divinylbenzene PL-GEL™ (Polymer Industries Inc., Amherst, Mass.) having a diameter of approximately 5 μm with a pore size of 50 Å.

The liquid solvent in the preferred embodiment is tetrahydrofuran (THF) but almost any liquid solvent can be used with this invention. The solvent is selected to be compatible with the packing material chosen, and the intended use of the column.

After the slurry is prepared, it is preferably allowed to sit for a period of time (e.g. 2 hours), so that the polymeric material can swell prior to use. After swelling, the slurry is preferably suspended by ultrasonication for a short period of time (e.g. 5 minutes). The slurry is then introduced to a slurry reservoir. The purpose of the slurry reservoir is to contain a large quantity of slurry which may be pressurized so that the slurry may be continuously fed into a microcolumn at a constant pressure. The size and length of the column to be filled as well as the concentration of the slurry dictate how large the reservoir needs to be. Accordingly, the slurry reservoir can take many forms. In a preferred embodiment, the slurry reservoir comprises a 6 cm×2 mm inside diameter×6 mm outside diameter stainless steel tube equipped with ¼" to ¹⁄₁₆" reducing fittings to secure the reservoir to the microcolumn.

After filling the reservoir with slurry, a pumping means is attached to slurry reservoir at the end opposite the microcolumn. The pumping means then operates to deliver the slurry from the slurry reservoir to the microcolumn. The slurry enters the microcolumn and is forced down to the retaining means. The retaining means allows the solvent to pass, but retains the packing material, forming a bed of uniformly packed material. This bed of packing material continues to accumulate along the length of the column as long as the pumping means is operating. Preferably, the microcolumn is vibrated as the slurry is added. Vibrating the microcolumn helps to prevent any bridges of packing material from forming above the bed surface. Vibrating the column can be accomplished using such devices as a mechanical vibrator or a sonic bath.

The pumping means can be any number of commercially available pumps capable of delivering liquids under pressure. One example of a suitable pumping means is an Isco model μLC-500 solvent delivery system. The pumping means is preferably operated at a constant pressure high enough to force the slurry into the microcolumn, and less than approximately 680 atm. More preferably it is operated at a constant pressure within the range of 170–400 atm. Still more preferably it is operated at a pressure within the range of 170–250 atm.

The pumping means continues to deliver the slurry at the selected pressure until a sufficient length of the microcolumn has been filled with packing material. The intended use of the column will dictate what length of column should be filled. The method is capable of filling columns as short as 1 cm to as long as several meters in length. In a preferred embodiment the packing material is allowed to accumulate to a length of slightly more than 1 meter.

After a sufficient length of the microcolumn has been filled with packing material, the pumping means is turned off. The pressure in the microcolumn will gradually approach the ambient pressure as the solvent continues to exit past the retaining means. Once the pressure within the column is near ambient pressure the columns were disconnected from the slurry reservoir and cut to a desired length.

It is important to prevent the microcolumns from drying out, as the polymeric packing swells in the solvent. Thus if allowed to dry voids within the column are likely to develop reducing column performance.

The following examples are for size exclusion chromatography microcolumns. It should be appreciated that the method can be used to pack any microcolumn with a polymeric material, regardless of the chromatographic application for which the microcolumn is eventually used.

EXAMPLE 1

To evaluate the method, a microcolumn for size exclusion chromatography was prepared according to the method of the invention. The column was packed with particles of styrene-divinylbenzene PL-GEL™ of 5 μm particle diameters and 50 Å pore size, obtained from Polymer Industries Inc. of Amherst, Mass. The packing material was added to tetrahydrofuran (THF) to form a slurry having a ratio (milliliters of solvent to grams of packing material) of 20. The packing material was allowed to swell for 2 hours and then the slurry was suspended by ultrasonication for five minutes. The suspended slurry was then added to the slurry reservoir. The slurry was delivered at a constant pressure of 170 atmospheres to a fused silica microcolumn having an inner diameter of 250 μm and which had been equipped with a ceramic retaining means. The microcolumn was vibrated during the delivery of the slurry with a mechanical vibrator. The delivery of the slurry was stopped after slightly more than one meter of the fused silica tubing was filled with packing material. The solvent remaining in the column continued to exit through the retaining means, thereby allowing the column to decompress to ambient pressure. After decompression the column was cut to a length of one meter.

The column was evaluated using a system which comprised a syringe pump operated at a constant flow rate, an injection valve with a 60 nL internal loop volume, and an ultraviolet detector equipped with a modified detector cell having a 6 nL volume. FIG. 1 is a copy of a chromatogram obtained for a 60 nl sample comprising a series of varying molecular weight compounds. THF was used as the eluent at a flow rate of 0.65 μl/min. Specifically the peak labeled 11 represents polystyrene having a molecular weight of 2.2 million, peak 12 represents IRGANOX 1010™ having a molecular weight of 1178, peak 13 represents IRGANOX 1076™ having a molecular weight of 530, peak 14 represents CYANOSORB UV-531™ having a molecular weight of 326, peak 15 represents Triphenyl methane having a molecular weight of 244, peak 16 represents Biphenyl having a molecular weight of 154, and peak 17 represents Toluene having a molecular weight of 92.

The column's performance was then evaluated. Polystyrene having a molecular weight of 2.2 million was used to determine the exclusion volume ($t_o$) and toluene was used as the totally permeated probe. The column's performance was determined using reduced parameters as taught by J. C. Giddings, *Dynamics of Chromatography*, Marcel-Dekker, New York, N.Y., 1965, herein incorporated by reference. Column performance was determined by finding the minimum value of a plot of h vs v, where h and v were calculated using the following equations:

$$h = H/d_p = L/N(d_p)$$

where h=reduced plate height, H=plate height, $d_p$=particle size, L=column length, and N=plate number calculated either by using the Foley-Dorsey Approximation (J. P. Foley, J. G. Dorsey, 55 *Analytical Chemistry*, 730 (1983)) or by measuring the peak width at half height for the totally permeated probe (toluene); and $$v = \mu d_p / Dm$$

where v=reduced velocity, μ=linear velocity, Dm=diffusion coefficient in the mobile phase. The diffusion coefficient in the mobile phase Dm was estimated for Toluene to be $8.33 \times 10^{-6}$ using the Wilke Chang equation (C. R. Wilke, P. Chang, *Am. Inst. Chem. Eng. J.*, 1, 264 (1955)).

Column performance was also evaluated using the flow resistance factor (Φ), specific column permeability (K°), and separation impedance (E), as defined by the following equations:

$$\Phi = d p^2 \Delta P / \mu L \eta$$

where ΔP=pressure drop and η=eluent viscosity;

$$K° = dp^2/\Phi$$

$$E = h^2 \Phi$$

Results for the column prepared as stated for this example are as follows: minimum h value=2.6, Φ=480, K°=5.81× $10^{-10}$ cm² and E=2950.

EXAMPLES 2-10

A series of columns 30 cm in length were prepared in the same manner as in Example I, adjusting the pressure at which the slurry was introduced into the microcolumn and the slurry ratio as indicated in Table I. Each of the columns was evaluated using the same procedures as in Example I. The results of the evaluations are summarized in Table I.

TABLE I

| Example No | Packing pressure (atm) | Slurry Ratio | h (min) | Φ | K° (x $10^{-10}$ cm²) | E |
|---|---|---|---|---|---|---|
| 2 | 170 | 40 | 2.7 | 280 | 8.93 | 2040 |
| 3 | 170 | 20 | 2.9 | 300 | 8.33 | 2530 |
| 4 | 170 | 10 | 2.1 | 750 | 3.33 | 3210 |
| 5 | 270 | 40 | 2.4 | 510 | 4.90 | 2940 |
| 6 | 270 | 20 | 2.2 | 700 | 3.57 | 3330 |
| 7 | 270 | 10 | 2.2 | 800 | 3.12 | 3550 |

TABLE I-continued

| Example No | Packing pressure (atm) | Slurry Ratio | h (min) | Φ | K° (x $10^{-10}$ cm²) | E |
|---|---|---|---|---|---|---|
| 8 | 400 | 40 | 2.4 | 870 | 2.87 | 5010 |
| 9 | 400 | 20 | 2.1 | 1250 | 2.00 | 5500 |
| 10 | 400 | 10 | 2.1 | 1400 | 1.78 | 6820 |

As can be seen in Table I, the column which gave the lowest separation impedance (E) was the column packed at the lowest pressure (170 atm) with the highest slurry ratio (i.e. the most dilute). Furthermore, examination of the information in the table reveals a general trend of decreasing permeability (K°) with increasing packing pressure and decreasing slurry ratio. This may indicate that the packing material is becoming deformed (or crushed) during high pressure column packing.

EXAMPLE 11

In order to compare the performance of columns made according to the method of the present invention, a conventional sized column having an inner diameter of 8 mm and a length of 30 cm was obtained from Polymer Industries, Inc. This column was packed with styrene-divinylbenzene PL-GEL™ of 5-μm particle diameter and 50 Å just as in the columns prepared in Example 2. The column was evaluated according to the methods used for Examples 1 and 2. The results of the evaluation are as follows: The minimum h value in a plot of h vs. v was 3.2, Φ was equal to 490, K° was equal to $5.13 \times 10^{-10}$ cm², and E was equal to 4980.

EXAMPLE 12

The one meter column of Example 1 was operated at a high linear velocity so that it might be compared with the conventional sized SEC column described in Example 11. The flow rate was manipulated to yield the same retention time as the conventional sized column for a sample of polystyrene 580. FIG. 2 is a copy of the resulting chromatograms, with the chromatogram on the bottom being obtained by using a microcolumn of the present invention. The plate numbers obtained for the peak labeled 18 were 56,500 whereas the plate numbers obtained for the corresponding peak 19 were 18,800. Thus, for the smaller molecules the microcolumn of the present invention represent a 300% increase in efficiency over conventional-size columns without any increase in analysis time. An increase in efficiency was also observed for the higher oligomers (peaks 20-23 in FIG. 2), although the gain was not as dramatic. N=27,500 for peak 20, 17,600 for peak 21, 21,500 for peak 22 and 16,400 for peak 23.

Resolution in SEC is typically described using the resolution factor Dσ, where D is the slope of the linear portion of a calibration curve of Log mw vs. Elution time, and σ is the peak standard deviation, measured for a small molecule. Calibration curves obtained from polystyrene 580 are presented in FIG. 3, where curve 30 was obtained for the conventional-size column of Example 11, curve 31 was obtained from the microcolumn in Example 1 operated at high linear velocity, and curve 32 was obtained from the microcolumn of Example 1 operated at optimum linear velocity. The Dσ values obtained were 0.017 for the microcolumn operated at optimum linear velocity, 0.021 for the microcolumn operated at high linear velocity and 0.033 for the conventional-size column.

It will be appreciated that the above disclosed embodiments are suited to achieve the aforementioned objectives of the present invention. In addition, it is evident that those skilled in the art, once given the benefit of the foregoing disclosure, may make modifications of the specific embodiments described above without departing from the spirit of the invention. Such modifications are to be considered within the scope of the present invention which is limited solely by the scope and spirit of the appended claims.

What is claimed is:

1. A method of loading microcolumns with a packing material suitable for use in chromatography, comprising the steps of:

(a) obtaining a microcolumn having a first end and a second end, said microcolumn having an inner diameter of less than 1 mm;

(b) preparing a slurry containing the packing material and a liquid solvent, said slurry having a concentration of more than 10 milliliters of solvent per gram of packing material;

(c) placing a retaining means at the second end of the microcolumn, said retaining means being effective for retaining the packing material while allowing the liquid solvent to pass through said retaining means;

(d) vibrating the microcolumn while adding the slurry to the first end of the microcolumn at a constant pressure, said pressure being high enough to force the slurry into the microcolumn and less than about 680 atmospheres;

(e) stopping the addition of the slurry after a length of column suitable for use in chromatography has been filled;

(f) allowing the solvent to exit the second end of the column, so that the pressure inside the column gradually approaches the ambient pressure.

2. The method of claim 1 wherein the slurry concentration is from about 10 to about 40 milliliters of solvent per gram of packing material.

3. The method of claim 2 wherein the slurry concentration is from about 20 to about 40 milliliters of solvent per gram of packing material.

4. The method of claim 3 wherein the slurry concentration is from about 30 to about 30 milliliters of solvent per gram of packing material.

5. The method of claim 1 wherein the slurry is added to the first end of the microcolumn at a constant pressure of between 170 to 400 atmospheres.

6. The method of claim 5 wherein the slurry is added to the first end of the microcolumn at a constant pressure of between 170 and 250 atmospheres.

7. The method of claim 1 wherein the packing material is styrene-divinylbenzene particles.

8. The method of claim 7 wherein the styrene-divinylbenzene particles have a 5 μm particle size and a 50 Å pore size.

9. The method of claim 1 wherein the liquid solvent is tetrahydrofuran.

10. The method of claim 1 wherein the microcolumn has an inner diameter of approximately 250 μm.

11. The method of claim 1 wherein the column is filled to a length of more than 1 meter.

12. The method of claim 1 wherein the liquid solvent is the same as the eluent in a chromatographic application for which the column is intended.

* * * * *